(12) United States Patent
Monnier et al.

(10) Patent No.: US 10,501,402 B2
(45) Date of Patent: Dec. 10, 2019

(54) MULTIFUNCTIONAL ACRYLIC ETHER-ESTER PRODUCTS MODIFIED WITH CARBOXYLIC ANHYDRIDE OR ITS POLYACID FORM, PROCESS FOR PREPARING SAME AND ASSOCIATED CROSSLINKABLE COMPOSITIONS

(71) Applicant: Arkema France, Colombes (FR)

(72) Inventors: Guillaume P. Monnier, Avrigny (FR); Philippe Ciceron, Senlis (FR); Catherine M. Leroy, Lille (FR); Charles Bourrousse, Paris (FR)

(73) Assignee: Arkema France, Colombes (FR)

( * ) Notice: Subject to any disclaimer, the term of this patent is extended or adjusted under 35 U.S.C. 154(b) by 96 days.

(21) Appl. No.: 15/523,129

(22) PCT Filed: Oct. 13, 2015

(86) PCT No.: PCT/FR2015/052755
§ 371 (c)(1),
(2) Date: Aug. 17, 2017

(87) PCT Pub. No.: WO2016/066918
PCT Pub. Date: May 6, 2016

(65) Prior Publication Data
US 2017/0355660 A1    Dec. 14, 2017

(30) Foreign Application Priority Data

Oct. 29, 2014 (FR) ..................... 14 60384

(51) Int. Cl.
| C07C 69/80 | (2006.01) |
| C09D 4/06 | (2006.01) |
| C08G 63/676 | (2006.01) |
| C07C 67/29 | (2006.01) |
| C08F 122/10 | (2006.01) |
| C08F 222/10 | (2006.01) |

(52) U.S. Cl.
CPC .............. *C07C 69/80* (2013.01); *C07C 67/29* (2013.01); *C08F 122/105* (2013.01); *C08G 63/676* (2013.01); *C09D 4/06* (2013.01); *C08F 2222/1073* (2013.01)

(58) Field of Classification Search
CPC ...... C07C 69/80; C07C 67/29; C08F 122/105

USPC ......................................................... 524/854
See application file for complete search history.

(56) References Cited

U.S. PATENT DOCUMENTS

| 4,206,025 A | 6/1980 | Vrancken et al. |
| 5,096,938 A * | 3/1992 | Beck ...................... C07C 67/60 |
| | | 522/10 |

FOREIGN PATENT DOCUMENTS

JP    2010024380    2/2010

* cited by examiner

*Primary Examiner* — Hui H Chin
(74) *Attorney, Agent, or Firm* — Christopher R. Lewis

(57) ABSTRACT

The invention relates to a multifunctional acrylic product having a number-average functionality f of acrylate groups greater than 2.1, which is the product of reaction by esterification and by etherification, via Michael addition reaction, between a) a polyol or a mixture of polyols $R(OH)_m$ having a functionality m of at least 3 for a polyol alone or having an average functionality greater than 2.1 for a mixture of polyols, and b) the acrylic acid ($R_1OH$) in the presence of c) at least one cyclic polycarboxylic anhydride or of its polyacid form having a carboxy functionality z of at least 2 and up to 4, the ratio $r_1$ of number of carboxy groups of said anhydride or polyacid c) with respect to those of the acrylic acid b) $r_1=CO_2Hc/CO_2Hb$ being from 0.01 to 0.4 with overall $r=CO_2H/OH<1$, said acrylic product comprising in its composition both:
  units A) of oligoether-ester acrylate that are derived from a) and b) and
  units B) of oligoester acrylate that are derived from c),
said acrylic product being a mixture of acrylic products comprising at least one acrylic product p1 chemically linking, in its molecular structure, the two types of units A) and B) as defined above.

The invention also relates to a process for preparing said product, to crosslinkable compositions comprising same and to the use thereof in coatings, sealing, moulding or composite compositions, chemical sealing compositions, 3D printing compositions or compositions for 3D objects produced layer-by-layer. One particular advantage of these compositions is their low shrinkage despite their high functionality.

25 Claims, No Drawings

MULTIFUNCTIONAL ACRYLIC ETHER-ESTER PRODUCTS MODIFIED WITH CARBOXYLIC ANHYDRIDE OR ITS POLYACID FORM, PROCESS FOR PREPARING SAME AND ASSOCIATED CROSSLINKABLE COMPOSITIONS

CROSS-REFERENCE TO RELATED APPLICATIONS

This application is a U.S. national stage application under 35 U.S.C. § 371 of PCT/FR2015/052755, filed Oct. 13, 2015, which claims benefit to French patent application number 1460384, filed Oct. 29, 2014.

FIELD OF THE INVENTION

The present invention relates to novel multifunctional acrylic monomers which are acrylic oligoether-ester products based on a mixture of multifunctional acrylic products derived from the reaction of acrylic acid in deficit with a multifunctional polyol in the presence of a carboxylic anhydride or polycarboxylic acid in minor carboxy-equivalent proportions, relative to the acrylic acid, to a preparation process, to crosslinkable compositions based on said products, to uses of said acrylic products as multifunctional acrylic binders of high functionality for crosslinkable compositions of high crosslinking density and low shrinkage and more particularly for pigmented or non-pigmented coating compositions, in particular paints, varnishes, inks, adhesives or moulding, sealing or composite compositions or chemical sealing compositions, 3D printing compositions or compositions for 3D objects produced layer-by-layer, and to the corresponding crosslinked final products.

BACKGROUND OF THE INVENTION

Multifunctional acrylic monomers of high functionality, of at least three and possibly ranging up to six, in terms of acrylic groups already exist and are used in coating applications such as varnishes or inks for increasing the crosslinking density and the performance levels related to this increase, such as chemical resistance or hardness.

However, the existing acrylic multifunctional monomers lead to poor flexibility, in particular for use in coatings, said flexibility being defined here in terms of resistance to folding determined by the folding test on a cylindrical support. Thus, the hardness/flexibility compromise is poor, as is the adhesion to substrates, for example in applications for coatings such as varnishes or inks. This is essentially caused by an excessively high degree of crosslinking (which may be expressed by a density of crosslinking nodes per unit of weight) and shrinkage related to the large number of reacted unsaturations. Moreover, these monomers are based on specific multifunctional polyols such as polyol diethers of lower functionality, for example ditrimethylol propane (DiTMP) or dipentaerythritol (DiPE), these products being difficult to access and costing many times that of the starting polyols, for example for DiTMP relative to trimethylol propane (TMP) or for DiPE relative to pentaerythritol (PE). A practical, simpler and less expensive solution is thus sought, thus using starting polyols such as TMP or PE, said solution simultaneously needing to solve the technical problems and drawbacks observed above with the existing products.

The possible recourse to alkoxylation of said starting polyols, which would make it possible to reduce the crosslinking density of the products obtained, moreover brings about a loss of reactivity, which is unacceptable since reactivity is one of the essential required properties, if not the essential property of these monomers.

SUMMARY OF THE INVENTION

The solution of the present invention overcomes these drawbacks with novel acrylic products having high functionalities, without using sophisticated and expensive raw materials, such as polyethers or dendrimer structures, but only starting with base polyols commonly used in chemistry and ensuring a crosslinking density for the final products obtained that is sufficient and controlled without being too high and with a significantly lower shrinkage, with a markedly improved compromise between hardness and flexibility as defined above and a markedly improved adhesion. More particularly, the solution of the present invention targets multifunctional acrylic (MFA) oligomers of high functionality as a replacement for the standard MFA acrylic oligomers, providing a high reactivity which can be defined as corresponding to the minimum speed of passage under a UV lamp (120 W/cm$^2$ fusion lamp) to have a coating which is not tacky to the touch of at least 25 m/min, and a higher hardness which can be defined as greater than or equal to 150 according to the Persoz method according to ISO 1522 and having a flexibility of less than 32 mm according to ISO 1519 (methods as defined in the experimental section), this being without the use of aromatic structures based on bisphenol A (BPA) which are well known for obtaining high hardnesses to the detriment of flexibility.

The solution of the present invention consists of an acrylic product which is a mixture of products comprising linear and branched oligo(ether-ester)s of controlled structure and composition starting from common polyols and acrylic acid and in the presence of at least one cyclic carboxylic anhydride or of its polyacid form, in minor carboxy-equivalent proportions relative to the acrylic acid with $r1=CO_2H$ anhydride/$CO_2H$ acrylic acid ranging from 0.01 to 0.4, preferably from 0.05 to 0.35 and more preferentially from 0.1 to 0.3, with a high and perfectly controlled mean functionality of acrylates by successive reactions of esterification and etherification by Michael addition and chain extension which is controlled, by formation of diesters based on said carboxylic anhydride. Branched structures of high functionality can be formed by sufficient lengthening via etherification by Michael addition and by esterification by the cyclic carboxylic anhydride or its polycarboxylic acid form and thus enable both high functionality and a sufficient crosslinking density without any particular shrinkage or any adhesion problems or any hardness or any flexibility compromise, and in particular a high reactivity and a high hardness as already defined above. The lengthening by etherification (by Michael addition) is controlled by the mole ratio of acrylic acid to the hydroxyl (OH) groups of said polyol, the carboxy groups of the acrylic acid and of said anhydride or of its polyacid form being in deficit relative to said OH groups and resulting in the overall ratio $r=-CO_2H/OH<1$, more particularly less than 0.97.

Among the advantages of this solution relative to the prior art, mention may be made of the following:
very good control of a poly(ether-ester) acrylate (PEEA) structure of low viscosity, of low hydrophilicity (virtually all the hydroxyl groups are consumed) and of very high functionality while at the same time maintaining a moderate double bond density, this structure is controlled by controlling the ratios r and r1 defined above, and therefore by amounts of the reagents used and is barely dependent on the conversion, thereby guaranteeing a better reproducibility of the characteristics and performance levels of the production from one batch to another, this structure allows the production of photo-crosslinked films of high flexibility without losing hardness and more particularly with a high hardness as defined above, these products have a viscosity very much lower than that obtained by simple polyesterification with addition of a diacid as main reactant with said polyol or by polyetherification by simple dehydration, another particular and important advantage is their very simple and practical synthesis which requires only a single step, starting from a reactive mixture of a common polyol or of a mixture of common polyols and in the presence of a carboxylic anhydride or of its polyacid form in minor carboxy-equivalent proportions relative to the acrylic acid, with overall the carboxy groups of the acrylic acid and of said carboxylic anhydride or of its polyacid form being in stoichiometric deficit relative to the OH groups of said polyol, as sole reactants and with acid catalysis and heteroazeotropic reflux to extract the esterification water and without any need for separation/purification of the final product. In contrast with the common products which are known or described, for example in JP 2010024380, the product is not washed but just neutralized, resulting in a better carbon footprint by reduction of the effluents with the yield limited solely by the loss of the esterification water, the final hydroxyl number is very low, resulting in a low hydrophilicity relative to the water tolerance, or a high hydrophobicity, which minimizes the environmental impact, more particularly, a very high reactivity corresponding to a minimum speed of passage under a UV lamp of at least 25 m/min and a high hardness, i.e. of at least 150 in Persoz according to ISO 1522, and a flexibility not reaching 32 mm according to ISO 1519, with no use of structures of bisphenol A type, commonly used in the prior art to achieve such a hardness performance level.

Among the other advantages of the solution according to the present invention, mention may in particular be made of the fact that the product according to the invention is a mixture of acrylic products of well-controlled and reproducible structure and composition, obtained in a single step, which can be used directly as it is for the final application, without requiring expensive operations for the separation of by-products, with a preparation process that is simple and practical to implement. Another particular advantage of this final product is the fact that it has a molecular distribution with controlled presence of the starting acrylic monomer, which acts as reactive diluent for the application composition. Consequently, the final product generally does not require the addition of supplementary reactive diluent to adjust its viscosity. On the other hand, it is possible to use such a supplementary reactive diluent for the highest average molecular weights of the final product, this depending on the final application and on the required application viscosity. A particular advantage of said products of the invention is their low volume shrinkage despite their high acrylate functionality. This is specific to the present invention.

DETAILED DESCRIPTION OF THE INVENTION

The invention relates firstly to an acrylic product, in particular a multifunctional acrylic oligomer, which is the product of reaction of a polyol or of a specific mixture of polyols, and of acrylic acid in the presence of at least one carboxylic anhydride or of its polycarboxylic acid form in minor carboxy-equivalent proportions, relative to the acrylic acid, and with production of a mixture of acrylic multifunctional monomers and oligomers, by simultaneous reaction of esterification of the free hydroxyls with acrylic acid, of etherification, via Michael addition on the acrylic double bond and addition of acrylic acid, of said hydroxyl groups overall in excess relative to the carboxy and hydroxyl groups borne by the acrylate partial esters, and limited chain extension by condensation of said carboxylic anhydride or polyacid with said hydroxyls.

Said product of the invention is also defined independently and alternatively as the product which can be obtained by means of a specific process defined by specific process conditions.

Another subject of the invention relates to a process for obtaining said acrylic product as a mixture of acrylic products which are multifunctional acrylic oligomers.

Another subject covered by the present invention relates to a crosslinkable composition comprising at least one acrylic product as defined according to the present invention.

Next, the invention also covers the use of said acrylic product according to the invention as a multifunctional acrylic binder in crosslinkable compositions, in particular with a high crosslinking density and low shrinkage, more particularly in pigmented or non-pigmented coating compositions, in particular paints, varnishes, inks, or adhesives or moulding, sealing or composite compositions or chemical sealing compositions or 3D printing compositions or compositions for 3D objects produced layer-by-layer.

Finally, the invention covers final products obtained by using at least one acrylic product according to the invention or by crosslinking a crosslinkable composition of the invention comprising said acrylic product, said products being selected from: pigmented or non-pigmented coatings, in particular paints, varnishes, inks or adhesives or from moulding, sealing or composite compositions or chemical sealing compositions or 3D printing compositions or compositions for 3D objects produced layer-by-layer.

The first subject of the present invention therefore relates to a multifunctional acrylic product, in particular a multifunctional acrylic oligomer, characterized in that it has a number-average functionality f greater than 2.1, preferably of at least 2.5 and more preferentially from 2.75 to 20 acrylic groups and even more preferentially from 3 to 14 acrylic groups per mole of said product and in particular with a density of said acrylic groups DA ranging from 2 to 12 mmol per g of said product, said product being the product of reaction by esterification and by etherification, by Michael addition reaction, between:

a) a polyol $R(OH)_m$ or a mixture of polyols $R(OH)_m$, of functionality m of at least 3, preferably of 3 to 6, more preferentially of 4 to 6 for a single polyol present and a number-average OH functionality greater than 2.1, preferably greater than 2.3, more preferentially of at least 2.5 and up to 6, for a mixture of said polyols, and b) the acrylic acid represented by $R_1OH$, said reaction between a) and b) taking place in the presence of c) at least one cyclic carboxylic anhydride or of its polycarboxylic acid form $R_2(CO_2H)_z$, of carboxy group ($-CO_2H$) functionality z of at least 2 and ranging up to 4, preferably from 2 to 3, more preferentially 2, with:

the ratio $r_1$ of number of carboxy groups of said anhydride
c) relative to those of b) acrylic acid, $r_1=(CO_2H)_c/(CO_2H)_b$ ranging acid from 0.01 to 0.4, preferably from 0.05 to 0.35 and more preferentially from 0.1 to 0.3, the carboxy groups being overall in deficit relative to the hydroxyl groups of said polyol a), with $r=CO_2H/OH<1$, in particular less than or equal to 0.97, said acrylic product comprising in its composition both:
units A) of oligoether-ester acrylate that are derived from the reaction of a) and of b), formed by a Michael addition reaction:
of the OH groups of said polyol a) or
of OH groups of hydroxylated partial acrylates formed on the unsaturation of the acrylic acid b) or on the unsaturation of one of the acrylates formed by esterification with b) and simultaneous esterification with b) of said polyol a) and of said hydroxylated partial acrylates or (simultaneous esterification) with the carboxy groups of the carboxylated Michael adduct formed between a) and b), and
units B) of oligoester acrylates derived from c) by a reaction of esterification with said anhydride or with its polyacid form c) of said polyol a) or of said hydroxylated partial acrylates or of the hydroxylated ether-ester acrylates formed, said acrylic product being a mixture of acrylic products comprising at least one acrylic product p1 chemically linking, in its molecular structure, the two types of units A) and B) as defined above.

More particularly, the acrylic product according to the invention has an overall composition which can be represented by the following general average formula (I):

with a and b representing the average mole fraction of each unit A) and B) per overall average unit of said product and with a+b=1 and a/b ranging from 0.15 to 22, preferably from 0.5 to 10, more preferentially from 1 to 5, n being the number of repeat overall units (motifs) with average n per mole of said product
$n_{ave}$ ranging from 0.2 to 10, preferably from 0.35 to 8, more preferentially from 0.35 to 6 and even more preferentially from 0.4 to 2.5.

It is obvious, as shown by the more detailed formulae, that the units A) and B) as defined above bear acrylate side groups.

According to one particular option, said acrylic product of the invention comprises said product p1 and said product p1 has a molecular structure defined according to general formula (II) below:

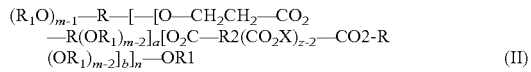

and with the presence of at least four products having a different n, corresponding to n=0 and n=1, n=2 and n=3 with:

$R_1$ being the acryloyl radical, R being the residual radical of said polyol $R(OH)_m$ or representing an average radical of a mixture of polyols,
$R_2$ being the residue of valency z of said anhydride or its polycarboxylic acid form and X being $-R(OR_1)_{m-1}$ with X possibly being essentially, i.e. more than 95%, $-R(OR_1)_{m-1}$ and the rest (less than 5%) of X being H, in particular with an acid number not exceeding 15 mg KOH/g, more particularly not exceeding 10 mg KOH/g, n being the number of repeat units and
a and b being the respective mole fractions of the particular units in the overall repeat unit with the ratio a/b ranging from 0.15 to 22, preferably from 0.5 to 10, more preferentially from 1 to 5.

According to an even more particular option, said product of the invention comprises, in addition to said product p1, an oligoether-ester acrylate product p2 based on units A) of general formula (III) below:

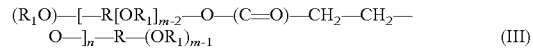

with the presence of at least four products having a different n and corresponding to n=0 and n=1, n=2 and n=3 and n being the number of repeat units.

According to a more specific option, it comprises, in addition to said product p1, an oligoester acrylate product p3 of general formula (IV) below:

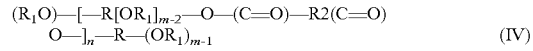

with the presence of at least four products having a different n and corresponding to n=0 and n=1, n=2 and n=3 and n being the number of repeat units.

According to an even more specific and preferred option, said product comprises a product p2 as defined according to formula (III) described above, said product p1 is as defined according to formula (II) as defined above and the three products p1, p2 and p3 as defined each comprise at least a fifth product corresponding to n=4 and, as an option, an additional product corresponding to n=5.

More particularly, said product p1 has the following general formula (V):

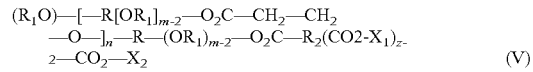

with $R_2$ being the radical of valency z corresponding to said carboxylic anhydride or to said polycarboxylic acid and $X_1$ and $X_2$ possibly being identical or different and chosen from:
$-R(OR_1)_{m-1}$ or
$-R(OR_1)_{m-2}-[O-CH_2-CH_2-CO_2-R(OR_1)_{m-2}]_n-(OR_1)$ or
in part H, in particular with a corresponding acid number not exceeding 20, in particular not exceeding 15 mg KOH/g or
in part the residue of a monofunctional reactive blocking agent, in particular reactive with the residual carboxy group in particular by esterification of said residual carboxys having a residual acid number not exceeding 20, more particularly not exceeding 15 mg KOH/g.

Regarding the case where X, and/or $X_2$ are in part residual carboxy groups with the corresponding acid number not exceeding 20 mg KOH/g, in particular not exceeding 15, more particularly if the esterification reaction is incomplete with said anhydride or said polyacid, said monofunctional blocking agent may be a saturated or unsaturated monoepoxide. As an example of an unsaturated monoepoxide, mention may be made of glycidyl methacrylate and as a saturated monoepoxide, mention may be made of ether or ester derivatives of glycidyl respectively with an alcohol or a carboxylic acid.

More particularly, the overall molecular distribution in terms of n of said product is such that it represents at least 80% by weight for n ranging from 0 to 4 and no more than 20% by weight of said distribution for n being greater than 4, preferably with a number-average weight Mn of said product, measured by GPC in THF and expressed in polystyrene equivalents, ranging from 500 to 10000 and more preferentially from 600 to 6000. Said Mn of said product is calculated from average n as defined above, the average molecular weight of the overall repeat unit under consideration.

According to one particular option of said product according to the invention, said polyol a) has a functionality m for a polyol a) alone of at least 3, and said product comprises linear oligoether-ester acrylate products p2 according to general formula (III) and also at least one oligoether-ester acrylate product of branched structure (or comprising a branched chain). The term "branched structure" signifies, for the product under consideration, that there is at least one side link of the same nature, attached via a covalent bond to the main chain of said product.

Said acrylic product alternatively can be defined as the product that can be obtained by simultaneous or successive and alternating reactions between a) a polyol $R(OH)_m$ or a mixture of polyols $R(OH)_m$, having a functionality m of at least 3, preferably from 3 to 6, more preferentially from 4 to 6, for a polyol a) alone, or having a number-average functionality (with respect to m) greater than 2.1, preferably greater than 2.3, more preferentially of at least 2.5 and up to 6 for a mixture of polyols $R(OH)_m$ and b) the acrylic acid ($R_1OH$) in deficit relative to a), and in the presence of c) at least one cyclic carboxylic anhydride or of its polyacid form having a carboxy group functionality z ranging from 2 to 4, preferably from 2 to 3, more preferentially of 2, with an overall ratio $r=CO_2H/OH$ of less than 1, in particular greater than $[(m-1)*(r_1+1)]/[m*((r_1/2)+1)]$ and ranging up to 0.97, preferably greater than $1.05*[(m-1)*(r_1+1)]/[m*((r_1/2)+1)]$ and ranging up to 0.97 and more preferentially greater than $1.10*[(m-1)*(r_1+1)]/[m*((r_1/2)+1)]$ and ranging up to 0.97, with $r_1$ being the ratio of the carboxy groups of c) to the carboxy groups of b) acrylic acid, $r_1=(carboxy)_c/(carboxy)_b$, more particularly with z=2.

Said polyol a), alone or as a mixture, can be selected from polyol monomers and/or polyol oligomers with Mn for polyol oligomers not exceeding 700, preferably not exceeding 600. This value Mn for said polyol oligomers can be calculated from the OH number and from the functionality.

For a polyol a) which is a polyol monomer, it may be selected from: diethylene glycol, triethylene glycol, tetraethylene glycol, propylene glycol, dipropylene glycol, tripropylene glycol, tetrapropylene glycol, butane diol, neopentyl glycol, hexane diol, isosorbide, glycerol, trimethylol propane, pentaerythritol, ditrimethylolpropane, erythritol, xylitol, dipentaerythritol and sorbitol, including the alkoxylated derivatives of the polyols mentioned.

The polyol a) may be a polyol oligomer chosen from: polyether polyols, polyester polyols and hydroxylated, optionally alkoxylated, acrylic oligomers and in particular it is present as a mixture with at least one other polyol a), preferably a polyol monomer as defined above.

Preferably, when said polyol a) is alkoxylated, there are from 1 to 4 alkoxy units. A suitable polyol oligomer may be selected from: polyether polyols, polyester polyols, and hydroxylated acrylic oligomers. The hydroxylated acrylic oligomers may be, for example, copolymer oligomers based on hydroxyalkyl (meth)acrylates, with the content of said hydroxyalkyl (meth)acrylate fixing the functionality of said oligomer.

Said product of the invention can be obtained as already described above from a mixture of polyols a) as defined above.

According to one particular and preferred option of the product of the invention, in addition to said polyol a) having a functionality of at least 3, a second polyol different than the first having a functionality of at least 2, is present, this second polyol preferably being an oligoester diol, more preferentially comprising, as component in its repeat unit, said anhydride c) or its polyacid form. This option thus makes it possible to adjust the average functionality f and the compatibility between the components of the mixture of the acrylic products included in the acrylic product according to the invention, in particular the products as defined above according to p1, p2 or p3.

The term "carboxylic anhydride", as used in the present invention, means a cyclic carboxylic anhydride which may be aliphatic, cycloaliphatic or aromatic. Its polycarboxylic acid form corresponding to said anhydride, as used in the present invention, means the polycarboxylic acid corresponding to the opening (hydrolysis) of said carboxylic anhydride ring. This term "polycarboxylic acid" comprises in its meaning all the positional isomers of said polycarboxylic acid. In the case where the functionality z of said anhydride is an odd number, this means that the number of anhydride groups per molecule is equal to (z−1)/2 and that it also bears a carboxy group not associated with an anhydride ring.

In particular, said polycarboxylic anhydride c) or its polyacid form or isomer of the latter can be chosen from aromatic or cycloaliphatic or aliphatic polycarboxylic anhydrides or polycarboxylic acids, with it being possible for the cycloaliphatic or aliphatic structures to be unsaturated.

Said polycarboxylic anhydride or polyacid or said isomer of the latter may be aromatic and in particular selected from: (o-) phthalic anhydride, iso- or terephthalic acid, naphthenic anhydride or acid, trimellitic anhydride or acid, pyromellitic anhydride or pyromellitic acid, said anhydride or polyacid preferably having a functionality of 2.

Said anhydride or its polyacid form may also be selected from anhydrides and their cycloaliphatic diacid form, in particular from tetrahydrophthalic anhydride and acid, dihydrophthalic anhydride and acid, nadic (bicyclo (2,2,1) hept-5-ene-2, 3 dicarboxylic) anhydride and acid or cyclohexane dicarboxylic anhydride and acid.

According to one particular option, said anhydride or acid may be aliphatic and in particular chosen from maleic anhydride and acid, fumaric acid, itaconic anhydride and acid, and succinic anhydride and acid.

According to another particular option, said anhydride or acid is chosen from: (o-) phthalic anhydride, iso- or terephthalic acid, tetrahydrophthalic anhydride and acid, dihydrophthalic anhydride and acid, nadic anhydride and acid, maleic anhydride and acid, fumaric acid, itaconic anhydride and acid, and succinic anhydride and acid.

Said anhydride or its polyacid form may be a mixture of at least two anhydrides and/or polyacids c).

The chain length of said acrylic product according to the invention, including according to formulae (I), (II), (III), (IV) and (V), is characterized by the index n, which corresponds to the number of motifs (or units) A) or B) or average overall motifs (or units), the average motif being an average with respect to the units of type A) and B) given their molar proportions with respect to an average overall motif. Indeed, said product comprises linked ether-ester motifs (oligoether-esters) of type A, linked via successive Michael addition reactions, of an OH of said polyol on the acrylic acid, followed by the esterification of a residual OH (among m−1) of said polyol with another acrylic acid molecule of which the unsaturation may again be the subject of another Michael addition with an OH of another molecule of said polyol and linked ester motifs (or units) B) (oligoesters) linked via simultaneous reaction of said anhydride or of its polyacid form c) with the hydroxylated derivatives, including polyol a), hydroxylated partial acrylates and hydroxylated ether-ester acrylates, with additional or separate chain extension.

In particular, on the basis of the overall formula (I), the average indices n*a and n*b for each type of motif (unit) A) and B) can be estimated, in particular for z=2 for a total conversion, from the ratio of equivalents r=$CO_2$H/OH, the ratio r1=COOH anhydride/COOH acid and the functionality m of said polyol, by the following relationship:

$$n_{AVE}{*}a = [m{*}(1-r){*}(r_1+1)]/[m{*}r{*}((r_1/2)+1)+(1-m){*}(r_1+1)]$$

$$n_{AVE}{*}b = [m{*}r{*}r_1]/[m{*}r{*}((r_1/2)+1)+(1-m){*}(r_1+1)].$$

It is recalled that $n_{ave}{*}a + n_{ave}{*}b$ = average n ($n_{ave}$), since a+b=1.

An average functionality of acrylate groups f per acrylic product can be estimated (calculated) from the average n, $n_{ave}$, described above, from the functionality m of said polyol and from formula (I). Thus, f is defined, in particular for z=2, according to the following formula:

$$f = (m-2){*}n_{ave} + m.$$

It should be noted that, in the case of a mixture of two polyols having the functionalities m1 and m2 at respective mole ratios x1 and x2 (x1+x2=1) in said mixture, in this case, the functionality m to be used is the number average (molar) of the two polyols according to the following relationship:

$$m \text{ average} = x1{*}m1 + x2{*}m2.$$

In the case of a mixture of several polyols of index i of functionality $m_i$ and of mole ratios $x_i$ ($\Sigma_i x_i = 1$), the average functionality m will be equal to $m = \Sigma_i x_i {*} m_i$.

Preferably, n average, $n_{ave}$, ranges from 0.2 to 10, preferably from 0.35 to 8, more preferentially from 0.35 to 6 and even more preferentially from 0.4 to 2.5.

Said acrylic product of the invention may comprise acrylates of linear and/or branched structure. By definition, it cannot comprise a crosslinked structure, which is thus excluded. The term "linear structure" signifies here a linear chain with the possibility of bearing acrylate side groups and a branched chain derived from such a chain essentially by Michael addition on said side acrylates with the formation of ether-ester acrylate side links.

A second subject of the invention relates to a process for preparing said acrylic product as defined above according to the invention.

Said process for preparing a product as defined according to the invention comprises the following steps:

i) mixing in a reactor of said polyol a) of the acrylic acid b), of said anhydride or of said polyacid c) in proportions such that the overall mole ratio r=$CO_2$H/OH is less than 1, in particular greater than $[(m-1){*}(r_1+1)]/[m{*}((r_1/2)+1)]$ and ranging up to 0.97, preferably greater than $1.05{*}[(m-1){*}(r_1+1)]/[m{*}((r_1/2)+1)]$ and ranging up to 0.97 and more preferably greater than $1.10{*}[(m-1){*}(r_1+1)]/[m{*}((r_1/2)+1)]$ and ranging up to 0.97, with $r_1 = CO_2H_c/CO_2H_b$ being in the range of from 0.01 to 0.4, preferably from 0.05 to 0.35 and more preferentially from 0.1 to 0.3, more particularly for z=2 and in the presence of an acidic esterification catalyst and of a solvent forming an azeotrope with water, to form the reaction mixture, followed by ii) refluxing said reaction mixture, with simultaneous or successive and alternating reactions of esterification, by reaction of the acrylic acid b) and/or of said anhydride or polyacid c) with a hydroxyl of said polyol a) with formation of hydroxylated ester acrylates, and of etherification, via Michael addition reaction of a hydroxyl of said polyol or of said hydroxylated acrylate formed to an acrylate group and/or the acrylic acid b), and of esterification of the hydroxyl groups of said polyol and of said hydroxylated acrylates by said anhydride or diacid and gradual removal of the esterification water, with iii) continuation of the reaction until complete consumption of the OH functions ($I_{OH}$<20 mg KOH/g) by Michael addition reactions and esterification reactions with said acrylic acid b) and said anhydride or diacid c), iv) neutralization of said acidic catalyst before recovery of the final product, by removal of said solvent, without any other specific purification step required.

Another subject of the present invention relates to a crosslinkable composition, which comprises at least one product of the invention as described above or obtained by means of the process described above.

In the particular case where the calculated Mn of said acrylic product according to the invention is greater than 1000, preferably greater than 1500, said composition may comprise, in addition to said product, at least one reactive diluent, selected from acrylic monomers, preferably multifunctional acrylic monomers. The essential role of this diluent, if required, is to adjust the viscosity according to the final application.

More particularly, said composition is a crosslinkable composition, preferably crosslinkable via radiation, in particular via UV radiation in the presence of a photoinitiating system or via an electron beam (EB) in the absence of a photoinitiating system and/or via a thermal radical initiating system, in particular via a peroxide initiating system (P-cure) and/or via Michael addition (M-cure) or via a mixed system, in particular via dual crosslinking (dual cure), more particularly with the presence of at least two of the above-mentioned crosslinking systems.

The invention also covers the use of said product as defined above or obtained by means of a process as defined according to the invention, in crosslinkable compositions having a low degree of shrinkage, preferably in crosslinkable coating compositions. More particularly, such a use applies to pigmented or non-pigmented coating compositions, preferably from paints, varnishes, inks or adhesives or a moulding composition or a sealing composition or a composite composition or a chemical sealing composition or a 3D printing composition or a composition for 3D objects produced layer-by-layer.

Finally, the invention also relates to the crosslinked final product in particular chosen from crosslinked pigmented or non-pigmented coatings, preferably from paints, varnishes, inks or adhesives or final product chosen from moulded parts, seals, composites, chemical seals, 3D printing or 3D objects produced layer-by-layer, which final product results from the use of at least one product as defined above or obtained by means of a process as defined above according to the invention or from the crosslinking of a crosslinkable composition as defined above according to the invention.

The examples that follow are presented by way of illustration of the invention and of its performance levels and do not in any way limit the scope of the invention.

EXAMPLES

1) Starting Materials Used (See Table 1)

TABLE 1 starting materials used

| Trade name (REF) | Chemical name | Abbreviated name | Supplier | Function according to the invention | Functionality |
|---|---|---|---|---|---|
| TMP (Hydro) flakes | Trimethylol propane | TMP | BASF | Polyol a) | 3 |
| TEG | Triethylene glycol | TEG | SABIC | Polyol a) | 2 |
| Phthalic anhydride | Phthalic anhydride | PtAn | ATMOSA | Carboxylic anhydride c) | 2 |
| Glacial acrylic acid | Acrylic acid | AA | Arkema | Acrylic acid b) | 1 |
| Toluene | Toluene | Tol | TOTAL | Solvent | |
| MSA E-pure | Methanesulfonic acid | MSA | Arkema | Catalyst | |
| Extra pure hydroquinone | Hydroquinone | HQ | Rhodia | Inhibitor | |
| TIB KAT ® 256 | monobutyl tin oxide | MBTO | TIB Chemicals | Catalyst | |
| Darocur ® 1173 | 2-hydroxy-2-methylphenyl-propan-1-one | PI-1 | BASF | Photoinitiator | |
| Dipropylamine | Dipropylamine | DPA | BASF | Neutralizing agent vs catalyst | |
| Grilonit ® V51-31 | Trimethylol propane triglycidyl ether | TMPTGE | EMS | Neutralizing agent vs b) for reducing residual b) | |
| Triphenyl phosphine | Triphenyl phosphine | TPP | Rhodia | Catalyst COOH vs epoxy | |

2) Preparation of the Products According to the Invention 2.1) Procedure for Examples According to the Invention (Examples 1 to 2)

The ratios r and $r_1$ mentioned below in the examples correspond:

r, to the overall —$CO_2H$/—OH equivalent ratio, $r_1$, to the —$CO_2H$ originating from the anhydride or from the diacid c)/—COOH originating from the acrylic acid b) equivalent ratio or $r_1 = (CO_2H)_c/(CO_2H)_b$.

Example 1

Preparation of a Hydroxylated Polyester (Diol) A-1 Used as Polyol a)

669.1 g of triethylene glycol (4.461 mol), 329.9 g of phthalic anhydride (2.229 mol) and 1.0 g of monobutyltin oxide (0.005 mol) are introduced into a 1 litre reactor equipped with an anchor stirrer and on which is mounted a florentine tube with its condenser (device enabling continuous withdrawal of the esterification water), with a nitrogen inlet (for inerting) and with a thermometer probe.

The reaction mixture is gradually brought to two temperature stationary phases of 100 and 150° C. for five hours, then to 210-220° C. for 7 hours, until an acid number of less than 5 mg KOH/g is obtained at the time of stoppage of the esterification performed by cooling the reaction medium, after having distilled 4.0 ml of water.

A hydroxylated polyester product A-1 having the following characteristics is obtained:

Appearance: clear

Residual acidity or acid number of the product: 3.0 mg KOH/g

OH number of the product: 260 mg KOH/g

Mn calculated from the OH number and a functionality of 2, giving Mn=430 g/mol.

Preparation of a Poly Phthalo-Ether-Ester Acrylate B-1 According to the Invention Use is made, as polyol, of a mixture of polyols based on the hydroxylated polyol (diol) A-1 of example 1 and of TMP with r=0.926 and $r_1$=0.191.

264.8 g of acrylic acid (AA) (3.678 mol), 212.3 g of polyester diol A-1 of example 1 (0.494 mol), 167.1 g of trimethylolpropane (TMP) (1.247 mol), 51.9 g of phthalic anhydride (0.351 mol), 250.7 g of toluene, 10.3 g of methanesulfonic acid in aqueous solution at 70% (MSA-aq) (0.075 mol), and 3.7 g of hydroquinone (HQ) (0.003 mol) are introduced into a 1 litre reactor equipped with an anchor stirrer and on which is mounted a florentine tube with its condenser (device enabling continuous withdrawal of the esterification water under solvent reflux), with an air inlet (air sparge) and with a thermometer probe.

The reaction mixture is refluxed for ten hours, thus passing from a temperature of 105° C. (starting of boiling) to 115° C., until a low acid number<15 mg KOH/g is obtained at the time of stoppage of the esterification performed by cooling the reaction mixture, after having distilled 75 ml of water.

This organic phase is neutralized at 50° C. by adding 10.6 g of dipropylamine (0.105 mole) and with stirring for 1 h before distillation under vacuum at 80-95° C. and 200-100 millibar until complete removal of the solvent with a residual toluene<0.1%. 25.5 g of trimethylolpropane triglycidyl ether (0.084 mol) and 3.1 g of triphenyl phosphine (0.012 mol) are then added and the temperature is then gradually raised to 13° C. and maintained until a residual acid number<10 mg KOH/g is obtained.

A polyphthalo(ether-ester) acrylate product B-1 having the following characteristics is obtained:
Appearance: clear
Turbidity: 9%
Viscosity at 25° C.: 8 Pa·s
Residual acidity or acid number of the product: 7 mg KOH/g
OH number of the product: <20 mg KOH/g.

The molecular characteristics of B-1 are given in table 2 below.

A formulation F-1 having the following percentage composition is prepared by simple cold mixing:
B-1: 96%
PI-1: 4%

Characteristics of Formulation F-1
Reactivity: 30 m/min
Persoz hardness: 180 s
Flexibility: 20 mm
Resistance to acetone: >300 s Example 2

Preparation of a Polyphthalo-Ether-Ester Acrylate B-2 According to the Invention TMP is used as polyol a), with r=0.836 and $r_1$=0.235.

324.8 g of acrylic acid (AA) (4.511 mol), 297.6 g of trimethylolpropane (TMP) (2.221 mol), 78.4 g of phthalic anhydride (0.529 mol), 244.3 g of toluene, 13.7 g of methanesulfonic acid in aqueous solution at 70% (AMS-aq) (0.100 mol), and 1.5 g of hydroquinone (HQ) (0.001 mol) are introduced into a 1 litre reactor equipped with an anchor stirrer and on which is mounted a florentine tube with its condenser (device enabling continuous withdrawal of the esterification water under solvent reflux), with an air inlet (air sparge) and with a thermometer probe.

The reaction mixture is refluxed for 18 hours, thus passing from a temperature of 105° C. (start of boiling) to 115° C., until a low acid number<15 mg KOH/g is obtained at the time of stoppage of the esterification performed by cooling the reaction medium, after having distilled 95 ml of water.

This organic phase is neutralized at 50° C. with 14.2 g of dipropylamine (0.140 mol) and with stirring for 1 h before distillation under vacuum at 80-95° C. and 200-100 millibars until complete removal of the solvent (with residual toluene<0.1%). 22.3 g of trimethylolpropane triglycidyl ether (0.074 mol) and 3.3 g of triphenyl phosphine (0.013 mol) are then added and then the temperature is gradually raised to 125° C. and maintained until a residual acid number <10 mg KOH/g is obtained.

A polyphthalo(ether-ester) acrylate product B-2 having the following characteristics is obtained:

Appearance: clear
Turbidity: 10%
Viscosity at 50° C.: 20 Pa·s
Residual acidity or acid number of the product: 8 mg KOH/g
OH number of the product: <20 mg KOH/g.

The molecular characteristics of B-2 are given in table 2 below.

A formulation F-2 having the following percentage composition is prepared by simple cold mixing:
B-2: 96%
PI-1: 4%

Characteristics of Formulation F-2
Reactivity: 40 m/min
Persoz hardness: 290 s
Flexibility: 25 mm
Resistance to acetone: >300 s

TABLE 2

Molecular characteristics of the products B-1 and B-2 according to the invention

| REF | polyol a) | m or average m polyol a) | r = $CO_2H$/ OH | $r_1$ = $(CO_2H)_c$/ $(CO_2H)_b$ | $n_{ave}$*a average (calc) | $n_{ave}$*b average (calc) | A | $n_{ave}$ | Mn Calc (g/mol) | Mn GPC (Dalton) | average f/mol (calc) | DA mmol/ g (calc) |
|---|---|---|---|---|---|---|---|---|---|---|---|---|
| B-1 | TMP and A-1 | 2.72 | 0.926 | 0.191 | 0.335 | 0.337 | 0.50 | 0.672 | 599 | 1200 | 3.20 | 5.34 |
| B-2 | TMP | 3.00 | 0.836 | 0.235 | 1.831 | 0.885 | 0.67 | 2.716 | 1021 | 1900 | 5.72 | 5.60 |

Measurement and Characterization Methods

Determination of the Appearance:

The product is observed visually in daylight, through a 60 ml colourless glass bottle, to determine whether the product is:

Clear: low turbidity, it is comparable to water,
Hazy: not allowing a clear view through the bottle,
Cloudy: opaque bottle, no image can be seen through the bottle.

Determination of the Turbidity:

This is the percentage of scattered light relative to the total light transmitted by the sample contained in a 50 ml transparent tank (60 mm×40 mm×20 mm). The measurement is taken using a Hunterlab "Colorquest XE"® spectrocolorimeter.

Determination of the Noury Viscosity:

The time of travel, in the liquid to be characterized, of a steel ball under its own gravity is measured. Standard AFNOR XP.T51-213 specifies in particular the geometry of the container, the diameter of the ball (2 mm) and the path of the ball (104 mm). Under these conditions, the dynamic viscosity is proportional to the time of travel of the ball with one second corresponding to 0.1 Pa·s.

Determination of the Acid Number (AN):

The acidity of the product to be characterized is expressed in milligrams of potassium equivalent per gram of product. For this, an acid-based titration is carried out under the following conditions: a weight w of product (approximately exactly 10 g) is dissolved in 50 ml of a toluene/ethanol mixture (2 vol/1 vol). After total dissolution, titration is performed with a potassium hydroxide solution of normality N (approximately exactly 0.1 N). The equivalent point is detected by a combined electrode controlling an automatic burette (Metrohm "716 DMS Titrin"® automatic titration machine) delivering the equivalent volume $V_E$. After performing a blank test (50 ml of the toluene/ethanol mixture alone), which makes it possible to determine the equivalent volume $V_B$, the acid number (AN) is calculated via the following formula:

$$IA=(V_E-V_B)*N*56.1/w$$

with $V_E$ and $V_B$ in ml, N in mol/l and w in grams.

Determination of the Hydroxyl Number (IOH Number):

The hydroxyl number of the product to be characterized is expressed in milligrams of potassium hydroxide equivalent per gram of product. For this, an acid-base back titration after acetylation is performed under the following conditions: a weight w of product (approximately exactly 10 grams) is dissolved in exactly 10 ml of an acetylating mixture (para-toluenesulfonic acid monohydrate: 10 g; acetic anhydride: 60 g; ethyl acetate: 500 g). The resulting mixture is reacted in a closed Erlenmeyer flask for 30 minutes with stirring at 50° C. It is cooled to ambient temperature and then the excess acetic anhydride is hydrolyzed by adding 2 ml of water which is allowed to react for 2 minutes at ambient temperature, and then by adding 10 ml of hydrolyzing solution [pyridine/water] (3 vol/2 vol) which is allowed to react for 5 minutes at ambient temperature. 60 ml of [butanol/toluene] solvent (2 vol/1 vol) are then added. After homogenization, titration is carried out with a potassium hydroxide solution of normality N (approximately exactly 0.5 N). The equivalent point is detected by a combined electrode controlling an automatic burette (Metrohm "716 DMS Titrino"® automatic titration machine) delivering the equivalent volume $V_E$. After performing a blank test (10 ml of the acetylating mixture+2 ml of water+10 ml of hydrolyzing solution+60 ml of solvent) which makes it possible to determine the equivalent volume $V_B$, the hydroxyl number (OH number) is calculated via the following formulae:

$$OH\ number*=(V_B-V_E)*N*56.1/w$$

with $V_E$ and $V_B$ in ml, N in mol/l and w in grams.
OH number*: apparent hydroxyl number
OH number=OH number*+AN Determination of the Reactivity:

The formulation is applied as a 12 μm film on a contrast card (Leneta "Penoparc charts form 1B"®), and is then crosslinked using a 120 W/cm Hg Fusion lamp. The minimum passage rate (in m/min) necessary to obtain a touch-dry film is measured.

For the following hardness, flexibility and acetone resistance tests, the photo-crosslinked films are left in an air-conditioned room (T=23° C.) for 24 hours after crosslinking and before the measurements.

Determination of the Persoz Hardness According to Standard ISO 1522:

The formulation to be examined is applied as a 100 μm film on a glass plate and crosslinked with a 120 W/cm Hg Fusion lamp at a rate of 8 m/min.

The number of oscillations before damping of the oscillations (passing from 12° to 4° of amplitude) of a pendulum in contact with the coated glass plate is measured according to standard ISO 1522.

Determination of the Flexibility:

The formulation is applied as a 100 μm film on a 25/10 mm thick smooth steel plate (D-46® Q-Panel), and then crosslinked with a 120 W/cm Hg Fusion lamp at a rate of 8 m/min.

The coated plate is curved on cylindrical mandrels according to standard ISO 1519. The result is expressed as the value (in mm) of the smallest radius of curvature that can be imposed on the coating without it cracking or becoming detached from the support.

Determination of the Acetone Resistance:

The formulation is applied as a 12 μm film on a glass plate, and then crosslinked with a 120 W/cm Hg Fusion lamp at a rate of 8 m/min. The coating is rubbed with a cloth soaked with acetone. The result is the time (expressed in seconds) beyond which the film becomes detached and/or disintegrates.

Number-Average Molecular Weight Mn:

Mn calc: theoretical Mn calculated from $n_{AVE}*a$ and $n_{AVE}*b$ according to the method specified in the description, in particular for z=2:

$$Mn\ calc=M[R(OR_1)_m]+a*n_{AVE}*M[A]+b*n_{AVE}*M[B]$$
(in g/mol)

With:
Constant term: $M[R(OR_1)_m]=M[R(OH)_m]+54*m$
Motif A: $M[A]=M[R(OH)_m]+54*(m-1)$
Motif B: $M[B]=M[R(OH)_m]+M(R2)+54*(m-1)$ Mn measured: measured by GPC in THF as solvent and Mn expressed in polystyrene equivalents on columns calibrated with polystyrene standards.

Number-Average Functionality of the Product with Respect to Acrylates (See Description):

Acrylate density DA: from f as defined above by dividing by calculated Mn (see definition in the description).

$$DA=1000*f/Mn.$$

The invention claimed is:

1. Multifunctional acrylated product having a number-average functionality f greater than 2.1 acrylic groups per mole of said product and with a density of said acrylic groups DA ranging from 2 to 12 mmol per g of said product, said product being the product of reaction by esterification and by etherification, by Michael addition reaction, between:
  a) a polyol $R(OH)_m$ or a mixture of polyols $R(OH)_m$, of functionality m of at least 3 for a single polyol present and a number-average OH functionality greater than 2.1 for a mixture of said polyols, and
  b) the acrylic acid represented by $R_1OH$,
  said reaction between a) and b) taking place in the presence of c) at least one cyclic carboxylic anhydride or of its polycarboxylic acid form $R_2(CO_2H)_z$, of carboxy group ($-CO_2H$) functionality z of at least 2 and ranging up to 4:
    the ratio $r_1$ of number of carboxy groups of said anhydride c) relative to those of b) acrylic acid, $r_1=(CO_2H)_c/(CO_2H)_b$ ranging from 0.01 to 0.4,
    the carboxy groups being overall in stoichiometric deficit relative to the hydroxyl groups of said polyol a), with $r=CO_2H/OH<1$,
  wherein: R is the residual radical of a polyol of valency m or a mixture of polyols of valency m; $R_1$ is an acryloyl radical; and $R_2$ is the residue of valency z of said at least one cyclic carboxylic anhydride or of its polycarboxylic acid form;
  said acrylic product comprising in its composition both:
    units A) of oligoether-ester acrylate that are derived from the reaction of a) and of b), formed by a Michael addition reaction:
      of the OH groups of said polyol a) or
      of OH groups of hydroxylated partial acrylates formed on the unsaturation of the acrylic acid b) or on the unsaturation of one of the acrylates formed by esterification with b) and simultaneous esterification with b) of said polyol a) and of said b hydroxylated partial acrylates or simultaneous esterification with the carboxy groups of the carboxylated Michael adduct formed between a) and b), and units B) of oligoester acrylates derived from c) by a reaction of esterification with said anhydride or with its polyacid form c) of said polyol a) or of said hydroxylated partial acrylates or of the hydroxylated ether-ester acrylates formed, said acrylic product being a mixture of acrylic products comprising at least one acrylic product (p1) chemically linking, in its molecular structure, the units A) and B) as defined above, wherein the product has an overall composition represented by the following average general formula (I):

  (I)

with a and b representing the average mole fraction of each unit A) and B) per overall average unit of said product and with a+b=1 and a/b ranging from 0.15 to 22, n being the number of repeat overall units, with average n per mole of product $n_{ave}$ ranging from 0.2 to 10.

2. The product of claim 1, wherein the product comprises said product p1 and that said product p1 has a molecular structure defined according to general formula (II) below:

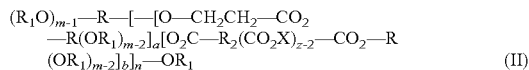  (II)

and with the presence of at least four products having a different n, corresponding to n=0 and n=1, n=2 and n=3 with:

$R_1$ being the acryloyl radical, R being the residual radical of said polyol $R(OH)_m$ or representing an average radical of a mixture of polyols, $R_2$ being the residue of valency z of said anhydride or its polycarboxylic acid form and X being —$R(OR_1)_{m-1}$ with X possibly being more than 95%, —$R(OR_1)_{m-1}$ and the rest less than 5% of X being H, with an acid number not exceeding 15 mg KOH/g, n being the number of repeat units and a and b being the respective mole fractions of the particular units in the overall repeat unit with the ratio a/b ranging from 0.15 to 22.

3. The product of claim 1 wherein it comprises, in addition to said product p1, the oligoether-ester acrylate product p2 based on units A) of general formula (III) below:

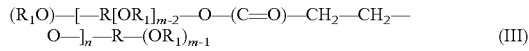  (III)

with the presence of at least four products having a different n and corresponding to n=0 and n=1, n=2 and n=3 and n being the number of repeat units.

4. The product of claim 1 wherein it comprises, in addition to said product p1, the oligoester acrylate product p3 of general formula (IV) below:

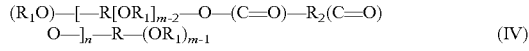  (IV)

with the presence of at least four products having a different n and corresponding to n=0 and n=1, n=2 and n=3 and n being the number of repeat units.

5. The product of claim 4, wherein it comprises a product p2 as defined according to formula (III) of claim 3, said product p1 is as defined according to formula (II) of claim 2 and the three products p1, p2 and p3 thus defined each comprise at least a fifth product corresponding to n=4 and, optionally, an additional product corresponding to n=5.

6. The product of claim 1 to 5, wherein said product p1 has the following general formula (V):

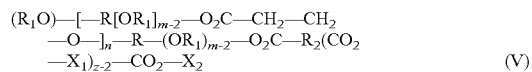  (V)

with $R_2$ being the radical having valency z corresponding to said carboxylic anhydride or to said polycarboxylic acid and $X_1$ and $X_2$ possibly being identical or different and chosen from:

—$R(OR_1)_{m-1}$ or

—$R(OR_1)_{m-2}$—[O—$CH_2$—$CH_2$—$CO_2$ —$R(OR_1)_{m-2}]_n$—$(OR_1)$ or in part H or in part the residue of a reactive blocking agent chosen from a monofunctional reactive blocking agent, reactive with the carboxy group.

7. The product of claim 1 wherein the overall molecular distribution in terms of n of said product is such that it represents at least 80% by weight for n ranging from 0 to 4 and no more than 20% by weight of said distribution for n being greater than 4, with a number-average weight Mn of said product, measured by GPC in THF and expressed in polystyrene equivalents, ranging from 500 to 10000.

8. The product of claim 1 wherein said polyol a) has a functionality m for polyol a) alone of at least 3 and that said product comprises linear oligoether-ester acrylate products p2 according to general formula (III) and also at least one oligoether-ester acrylate product of branched structure.

9. Acrylated product, wherein it can be obtained by simultaneous or successive and alternating reactions between a) a polyol $R(OH)_m$ or a mixture of polyols $R(OH)_m$, having a functionality m of at least 3 for a polyol a) alone, or having a number-average functionality with respect to m greater than 2.1 for a mixture of polyols $R(OH)_m$ and b) the acrylic acid ($R_1OH$) in stoichiometric deficit relative to a), and in the presence of c) at least one cyclic carboxylic anhydride or of its polyacid form having a carboxy group functionality z ranging from 2 to 4, with an overall ratio r=$CO_2H/OH$ of less than 1 with $r_1$ being the ratio of the carboxy groups of c) to the carboxy groups of b) acrylic acid, $r_1$=(carboxy)$_c$/(carboxy)$_b$, wherein R is the residual radical of a polyol of valency m or a mixture of polyols of valency m and $R_1$ is an acryloyl radical.

10. The product of claim 1 wherein said polyol a) is selected from polyol monomers and/or polyol oligomers with Mn for polyol oligomers not exceeding 700.

11. The product of claim 10, wherein said polyol is a polyol monomer and selected from: diethylene glycol, triethylene glycol, tetraethylene glycol, propylene glycol, dipropylene glycol, tripropylene glycol, tetrapropylene glycol, butanediol, neopentyl glycol, hexanediol, isosorbide, glycerol, trimethylolpropane, pentaerythritol, ditrimethylolpropane, erythritol, xylitol, dipentaerythritol and sorbitol, including the alkoxylated derivatives of the polyols mentioned.

12. The product of claim 10, wherein said polyol is a polyol oligomer chosen from polyether polyols, polyester polyols, and hydroxylated acrylic oligomers which are optionally alkoxylated.

13. The product of claim 1 wherein, in addition to said polyol a) having a functionality of at least 3, a second polyol different from the first and having a functionality of at least 2 is present, this second polyol being an oligoester diol, optionally comprising, as component in its repeat unit, said anhydride c) or its polyacid form.

14. The product of claim 1 wherein said polycarboxylic anhydride c) or its polyacid form or isomer of the latter is chosen from aromatic or cycloaliphatic or aliphatic polycarboxylic anhydrides or polycarboxylic acids, with the cycloaliphatic or aliphatic structures possibly being unsaturated.

15. The product of claim 14, wherein said polycarboxylic anhydride or polyacid or said isomer of the latter is aromatic and in particular selected from: (o-) phthalic anhydride, iso- or terephthalic acid, naphthenic anhydride or acid, trimellitic anhydride or acid, pyromellitic anhydride or pyromellitic acid.

16. The product of claim 14, wherein said anhydride or its polyacid form is cycloaliphatic and selected from tetrahydrophthalic anhydride and acid, dihydrophthalic anhydride and acid, nadic (bicyclo (2,2,1) hept-5-ene-2,3-dicarboxylic) anhydride and acid or cyclohexanedicarboxylic anhydride and acid.

17. The product of claim 14, wherein said anhydride or acid is aliphatic and chosen from: maleic anhydride and acid, fumaric acid, itaconic anhydride and acid, and succinic anhydride and acid.

18. The product of claim 14, wherein said anhydride or acid is chosen from: (o-) phthalic anhydride, iso- or terephthalic acid, tetrahydrophthalic anhydride and acid, dihydrophthalic anhydride and acid, nadic anhydride and acid, maleic anhydride and acid, fumaric acid, itaconic anhydride and acid, and succinic anhydride and acid.

19. The product of claim 1 wherein said anhydride or polyacid is a mixture of at least two anhydrides or polyacids c).

20. Process for preparing the product of claim 1, comprising:
   i) mixing in a reactor of said polyol a), of the acrylic acid b) and of said anhydride or of said polyacid c) in proportions such that the overall mole ratio $r=CO_2H/OH$ is less than 1, with $r_1=(CO_2H)_c/(CO_2H)_b$ being in the range of from 0.01 to 0.4 and in the presence of an acidic esterification catalyst and of a solvent forming an azeotrope with water, to form the reaction mixture, followed by
   ii) refluxing said reaction mixture, with simultaneous or successive and alternating reactions of esterification, by reaction of the acrylic acid b) and/or of said anhydride or polyacid c) with a hydroxyl of said polyol a) with formation of hydroxylated acrylate esters, and of etherification, via Michael addition reaction of a hydroxyl of said polyol or of formed hydroxylated acrylate, to an acrylate group and/or the acrylic acid b), and of esterification of the hydroxyl groups of said polyol and of said hydroxylated acrylates by said anhydride or diacid and gradual removal of the esterification water, with
   iii) continuation of the reaction until complete consumption of the OH functions meaning $I_{OH}<20$ mg KOH/g by Michael addition reactions and esterification reactions with said acrylic acid b) and said anhydride or diacid c),
   iv) neutralization of said acidic catalyst before recovery of the final product, by removal of said solvent, without any other purification step required.

21. A composition obtained by means of a process as defined according to claim 20.

22. The composition of claim 21, wherein, in the case where the calculated Mn of said product is greater than 1000, in addition to said product, the composition comprises at least one reactive diluent, selected from acrylic monomers.

23. The composition of claim 21 wherein the composition is capable to be crosslinked via radiation, by UV radiation in the presence of a photoinitiating system or by an electron beam (EB) in the absence of a photoinitiating system and/or by a thermal radical initiating system, and/or by Michael addition (M-cure) or by a mixed system.

24. The composition of claim 21 wherein the composition is a pigmented or non-pigmented coating composition or is a moulding composition or a sealing composition or a composite composition or a chemical sealing composition or a 3D printing composition or a composition for 3D objects produced layer-by-layer.

25. Crosslinked final product chosen from crosslinked pigmented or non-pigmented coatings, or chosen from moulded parts, seals, composites, chemical seals, 3D printing or 3D objects produced layer-by-layer, obtained by the process of claim 20.

* * * * *